US009266109B2

(12) United States Patent
Howell et al.

(10) Patent No.: US 9,266,109 B2
(45) Date of Patent: Feb. 23, 2016

(54) THERMAL CONTROL SYSTEM AND METHOD FOR CHEMICAL AND BIOCHEMICAL REACTIONS

(75) Inventors: James Richard Howell, Middlesbrough (GB); Benjamin Masterman Webster, Cleveland (GB)

(73) Assignee: IT-IS International Ltd. (GB)

( * ) Notice: Subject to any disclaimer, the term of this patent is extended or adjusted under 35 U.S.C. 154(b) by 761 days.

(21) Appl. No.: 12/936,307

(22) PCT Filed: Apr. 3, 2009

(86) PCT No.: PCT/GB2009/000899
§ 371 (c)(1), (2), (4) Date: Oct. 29, 2010

(87) PCT Pub. No.: WO2009/122191
PCT Pub. Date: Oct. 8, 2009

(65) Prior Publication Data

US 2011/0039711 A1 Feb. 17, 2011

Related U.S. Application Data

(60) Provisional application No. 61/042,672, filed on Apr. 4, 2008.

(51) Int. Cl.
*C12M 1/36* (2006.01)
*C12Q 1/68* (2006.01)
*B01L 7/00* (2006.01)

(52) U.S. Cl.
CPC ........... *B01L 7/52* (2013.01); *B01L 2300/1805* (2013.01); *B01L 2300/185* (2013.01); *B01L 2300/1894* (2013.01)

(58) Field of Classification Search
None
See application file for complete search history.

(56) References Cited

U.S. PATENT DOCUMENTS

| | | | | |
|---|---|---|---|---|
| 4,865,987 | A | 9/1989 | Niemela Seppo | |
| 5,240,857 | A | 8/1993 | Laehetkangas | |
| 5,504,007 | A | 4/1996 | Haynes | |
| 5,508,197 | A | 4/1996 | Hansen et al. | |
| 5,827,480 | A | 10/1998 | Haff et al. | |
| 2003/0136552 | A1 | 7/2003 | Beebe et al. | |
| 2005/0282224 | A1 | 12/2005 | Fouillet et al. | |
| 2006/0057032 | A1 | 3/2006 | Blok et al. | |
| 2008/0003649 | A1 * | 1/2008 | Maltezos et al. | 435/91.2 |

FOREIGN PATENT DOCUMENTS

| | | |
|---|---|---|
| EP | 0937832 | 8/1999 |

OTHER PUBLICATIONS

Pudur Jagadeenwaran et al., “A Simple and Easy-to-Assemble Device for Polymerase Chain Reaction”, vol. 8, No. 2, 1990.

Franco Rollo et al., “A Simple and low cost DNA amplifier”, Nucleic Acids Research, vol. 16, Nov. 7, 1988.

Hyung-Suk Kim and Oliver Smithies, “Recombinant fragment assay for gene targeting based on the polymerase chain reaction”, Nucleic Acids Research, vol. 16, Nov. 18, 1988.

* cited by examiner

*Primary Examiner* — Catherine S Hibbert
*Assistant Examiner* — Channing S Mahatan
(74) *Attorney, Agent, or Firm* — Hartman GlobalIP Law; Gary M. Hartman; Domenica N. S. Hartman

(57) ABSTRACT

A system (20) for a PCR reaction includes an array of reaction vessels mounted on a thermal mount (21). The thermal mount (21) is provided with a liquid path therein coupled to a cooling liquid input port (22), a heating liquid input port (23) and a liquid output port (24). A pump (38) is used to pump liquid from cooling liquid source (29) either along a cooling liquid path (28) to the cooling liquid input port (22), or via a heating liquid source (31), where the liquid is heated, and along a heating liquid path (30) to the heating liquid input port (23). A temperature sensor (34) measures the temperature of the thermal mount (21) and a processor (27) controls the pump, valves (26) at the input and output ports and valves (41-44) at either side of the pump (38), to control whether heating or cooling liquid is input to the thermal mount, and at what flow rate, in order to obtain the correct temperature of the thermal block (21).

22 Claims, 7 Drawing Sheets

THERMAL CONTROL SYSTEM AND METHOD FOR CHEMICAL AND BIOCHEMICAL REACTIONS

The present invention relates to a method and system for thermal control of chemical and/or biochemical reactions, such as, but not limited to, Polymerase Chain Reactions (PCR).

Many chemical and biochemical reactions are carried out which require highly accurately controlled temperature variations. Often, such reactions may need to go through several, or even many, cycles of varying temperature in order to produce the required effects.

A particular example of a reaction where a relatively large number of highly accurately controlled temperature varying cycles are required is in nucleic acid amplification techniques and in particular the polymerase chain reaction (PCR). Amplification of DNA by polymerase chain reaction (PCR) is a technique fundamental to molecular biology. PCR is a widely used and effective technique for detecting the presence of specific nucleic acids within a sample, even where the relative amounts of the target nucleic acid are low. Thus it is useful in a wide variety of fields, including diagnostics and detection as well as in research.

Nucleic acid analysis by PCR requires sample preparation, amplification, and product analysis. Although these steps are usually performed sequentially, amplification and analysis can occur simultaneously.

In the course of the PCR, a specific target nucleic acid is amplified by a series of reiterations of a cycle of steps in which nucleic acids present in the reaction mixture are denatured at relatively high temperatures, for example at 95° C. (denaturation), then the reaction mixture is cooled to a temperature at which short oligonucleotide primers bind to the single stranded target nucleic acid, for example at 55° C. (annealing). Thereafter, the primers are extended using a polymerase enzyme, for example at 72° C. (extension), so that the original nucleic acid sequence has been replicated. Repeated cycles of denaturation, annealing and extension result in the exponential increase in the amount of target nucleic acid present in the sample.

Variations of this thermal profile are possible, for example by cycling between denaturation and annealing temperatures only, or by modifying one or more of the temperatures from cycle to cycle.

DNA dyes or fluorescent probes can be added to the PCR mixture before amplification and used to analyse the progress of the PCR during amplification. These kinetic measurements allow for the possibility that the amount of nucleic acid present in the original sample can be quantitated.

Monitoring fluorescence during each cycle of PCR initially involved the use of a fluorophore in the form of an intercalating dye such as ethidium bromide, whose fluorescence changed when intercalated within a double stranded nucleic acid molecule, as compared to when it is free in solution. These dyes can also be used to create melting point curves, as monitoring the fluorescent signal they produce as a double stranded nucleic acid is heated up to the point at which it denatures, allows the melt temperature to be determined.

Of course, visible signals from dyes or probes are used in various other types of reactions and detection of these signals may be used in a variety of ways. In particular they can allow for the detection of the occurrence of a reaction, which may be indicative of the presence or absence of a particular reagent in a test sample, or to provide information about the progress or kinetics of a particular reaction.

Many such chemical or biochemical reactions take place in an apparatus having a number, sometimes a large number, of receptacles arranged in an array. In order not to affect the reaction, the receptacles are often formed from polypropylene as an array of wells in a plate. The wells are inserted into a metal block which is thermally controlled so that the wells are thermally controlled by thermal conductivity through the walls of the wells. Various ways of providing the required thermal control are known. One of the most common is by the use of Peltier modules that can be used to provide heating or cooling (depending on the direction of current flow through the module). Although Peltier modules are well known and will not be described in detail here, it should be noted that a Peltier module essentially consists of semiconductors mounted successively, which form p-n- and n-p-junctions. Each junction has a thermal contact with radiators. When switching on a current of one polarity, a temperature difference is formed between the radiators: one of them heats up and operates as a heatsink, the other cools down and operates as a refrigerator.

However, Peltier modules provide a number of disadvantages when used for accurate, repetitive thermal cycling because they are not designed, in the first instance, for such thermal cycling. Firstly, because the Peltier module is itself thermally conductive, there is a loss of power through the device. Secondly, current reversal causes dopant migration across the semiconductor junction, which is not symmetrical, hence the junction effectively loses its function as a junction between different semiconductors over time. Furthermore, repetitive temperature changes cause repetitive expansion and contraction cycles, which are not in themselves symmetric in a Peltier module. Since the Peltier module in thermal contact with the metal block holding the wells and is itself often formed with different metals, which expand/contract at different rates, mechanical problems develop. These are mitigated by mechanically clamping the modules at high pressures, but the mechanical problems still exist. Finally, it due to the nature of the operation of the Peltier module, hot and cold spots form on the surfaces thereof, which require large copper or silver heatsinks to average the heating, which again provide more mechanical problems.

As an alternative to Peltier modules, it has been suggested (in BioTechniques at pages 150-153 in Vol. 8, No. 2 (1990) by Pudur Jagadeeswaran, Kavala Jayantha Rao and Zi-Qiang Zhou in a paper entitled "A Simple and Easy-to-Assemble Device for Polymerase Chain Reaction) to use water provided in three different reservoirs at three desired temperatures. A pump is used to pump the water at the desired temperature to/from the appropriate reservoir to a water jacket surrounding the PCR device to heat/cool the device to that temperature. However, this system is limited by the number of reservoirs and cannot achieve fast temperature cycling. Another water-based temperature control system is known from a paper entitled "A simple and low cost DNA amplifier" by Franco Rollo, Augusto Amici and Roberto Salvi published in Nucleic Acids Research, Volume 16 number 7 1988 at pages 3105-3106. In this case, two reservoirs at appropriate temperatures are used, but, again, the temperatures of the device are limited to the temperatures of the water In the reservoirs. A similar system was also described by Hyung-Suk Kim and Oliver Smithies in a paper entitled "Recombinant fragment assay for gene targeting based on the polymerase chain reaction" published in Nucleic Acids Research, Volume 16 number 18 1988 at pages 8887-8903. In this case, however, the temperature range is extended to three temperatures, made by possible mixing of the water from the two reservoirs.

Nevertheless, it will be apparent that the above known systems have a number of disadvantages, at least some of which aspects of the present invention are intended to overcome, or at least mitigate, either individually, or in combination.

Accordingly, in a first aspect of the present invention, there is provided a thermal control system for controlling temperature of at least one reaction vessels in which chemical and/or biochemical reactions may take place, the temperature being controlled between at least a highest predetermined temperature and a lowest predetermined temperature, the system comprising a thermal mount for receiving the array of reaction vessels, one or more thermal sensors for sensing the temperature of one or more of the thermal mount, the reaction vessel(s) or the contents thereof, a heating liquid path having a liquid therein, the hot liquid path extending between the thermal mount and a heating element for heating the liquid to a temperature at least as high as the highest predetermined temperature, a cold liquid path having a liquid therein, the cold liquid path extending between the thermal mount and a cooling element for cooling the liquid to a temperature at least as low as the lowest predetermined temperature, means for causing the liquids in the hot and cold liquid paths to move between the thermal mount and the respective heating and cooling elements, and a controller coupled to the thermal sensor(s) for controlling movement of the liquids in the hot and cold liquid paths to and from the thermal mount and the respective heating and cooling elements in accordance with the sensed temperature so that the temperature of the reaction vessels(s) reaches or is maintained at a desired temperature for a desired amount of time.

In one embodiment, the heating element includes a heat source. Alternatively or additionally, the heating element includes a hot thermal ballast.

Similarly, in one embodiment, the cooling element includes a cooling source. Alternatively or additionally, the cooling element includes a cold thermal ballast.

The thermal mount can comprise a thermally conductive material.

In a preferred embodiment, the means for causing the liquids in the hot and cold liquid paths to move comprises at least one pump.

Further preferably, wherein the reaction vessel(s) forms part of an array of a plurality of reaction vessels.

The hot liquid path can comprise a closed liquid path arranged to pass through or adjacent the heating element so that the liquid therein is heated to a temperature at least as high as the highest predetermined temperature and to pass through or adjacent the thermal mount so that the hot liquid is used to heat the thermal mount, and thereby to cool down as it passes through the thermal mount.

Similarly, the cold liquid path can comprise a closed liquid path arranged to pass through or adjacent the cooling element so that the liquid therein is cooled to a temperature at least as low as the lowest predetermined temperature and to pass through or adjacent the thermal mount so that the cold liquid is used to cool the thermal mount, and thereby to heat up as it passes through the thermal mount.

Preferably, the hot liquid path and the cold liquid path are the same path through or adjacent at least part of the thermal mount. Alternatively or additionally, the hot liquid path and the cold liquid path are separate paths through or adjacent at least part of the thermal mount.

The controller preferably controls the temperature of the thermal mount by controlling the flow of the liquids in the hot and cold liquid paths to the thermal mount. In a preferred embodiment, the controller controls the temperature of the reaction vessels(s) by varying the flow rates of the liquids in the hot and cold liquid paths. The controller can control the temperature of the reaction vessel(s) by stopping and starting the flow of the liquids in the hot and cold liquid paths.

Further preferably, wherein the hot and/or cold liquid paths include a plurality of sub paths within the thermal mount and/or within respective heating and cooling elements.

According to a second aspect, the invention provides a method of controlling the temperature of at least one reaction vessel in which chemical and/or biochemical reactions may take place mounted on a thermal block, the temperature being controlled between at least a highest predetermined temperature and a lowest predetermined temperature, the method comprising sensing the temperature of the thermal block, the reaction vessel(s) and/or the contents thereof, and selectively pumping a cooling liquid along a cooling liquid path to a cooling liquid input of the thermal block and/or a heating liquid along a heating liquid path to a heating liquid input of the thermal block, the heating liquid path extending between the thermal block and a heating element for heating the liquid to a temperature at least as high as the highest predetermined temperature, the cooling liquid path extending between the thermal block and a cooling element for cooling the liquid to a temperature at least as low as the lowest predetermined temperature, in accordance with the sensed temperature of the reaction vessel(s) so that the temperature of the thermal block reaches or is maintained at a desired temperature for a desired amount of time.

Preferably, the reaction vessel(s) form part of an array of a plurality of reaction vessels.

In one embodiment, the heating liquid path comprises a closed liquid path arranged to pass through or adjacent a heating element so that the liquid therein is heated to a temperature at least as high as the highest predetermined temperature and to pass through or adjacent the thermal block so that the heating liquid is used to heat the thermal block, and thereby to cool down as it passes through the thermal block.

Preferably, the cooling liquid path comprises a closed liquid path arranged to pass through or adjacent a cooling element so that the liquid therein is cooled to a temperature at least as low as the lowest predetermined temperature and to pass through or adjacent the thermal block so that the cooling liquid is used to cool the thermal block, and thereby to heat up as it passes through the thermal block.

The heating liquid path and the cooling liquid path can be the same path through or adjacent at least part of the thermal block, or can be separate paths through or adjacent at least part of the thermal block.

In a preferred embodiment, the temperature of the reaction vessel(s) is controlled by controlling the flow of the liquids in the heating and cooling liquid paths to the reaction vessel. The temperature of the reaction vessel can be controlled by varying the flow rates of the liquids in the heating and cooling liquid paths and/or by stopping and starting the flow of the liquids in the heating and cooling liquid paths.

Preferably, the hot and/or cold liquid paths include a plurality of sub-paths within the thermal block and/or within the respective heating and cooling elements.

The reaction may be a Polymerase Chain Reaction or other types of chemical reactions such as, for example, Ligase Chain Reaction, Nucleic Acid Sequence Based Amplification, Rolling Circle Amplification, Strand Displacement Amplification, Helicase-Dependent Amplification, or Transcription Mediated Amplification.

Embodiments of a system incorporating various aspects of the invention will now be more fully described, by way of example, with reference to the drawings, of which:

Figure 4A:
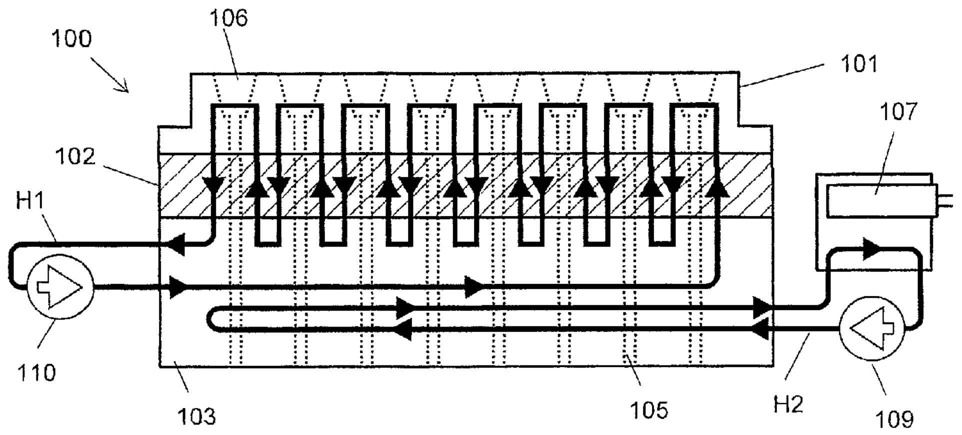
Figure 4B:
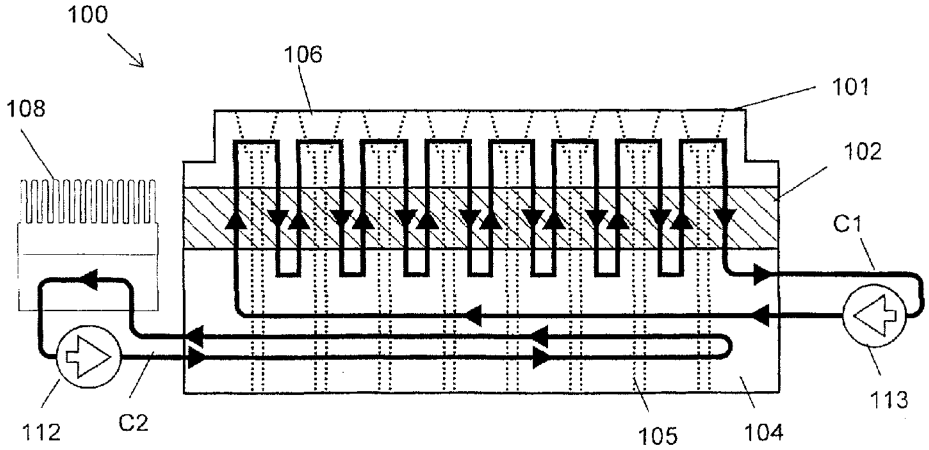
Figure 5A:
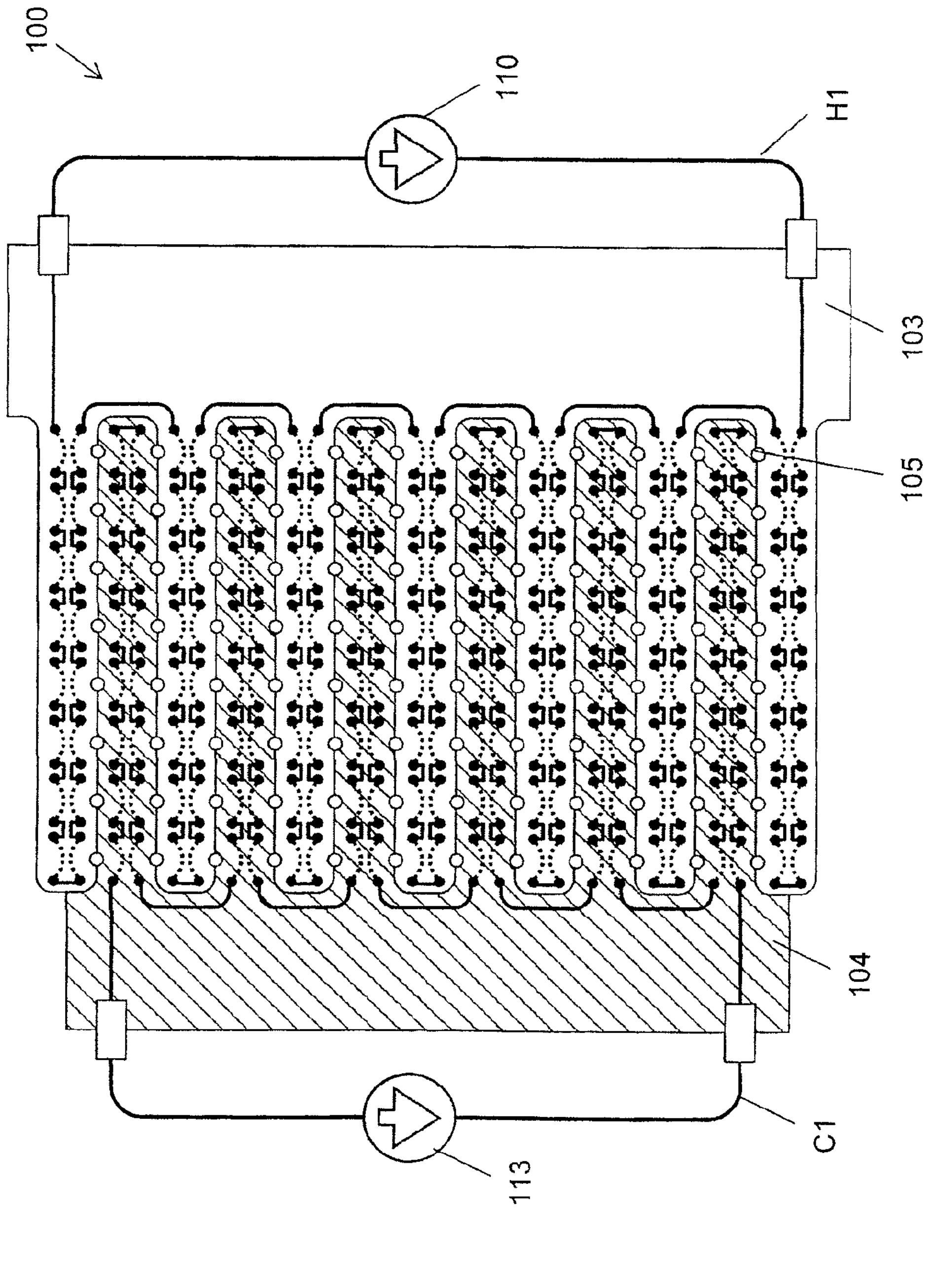
Figure 5B:
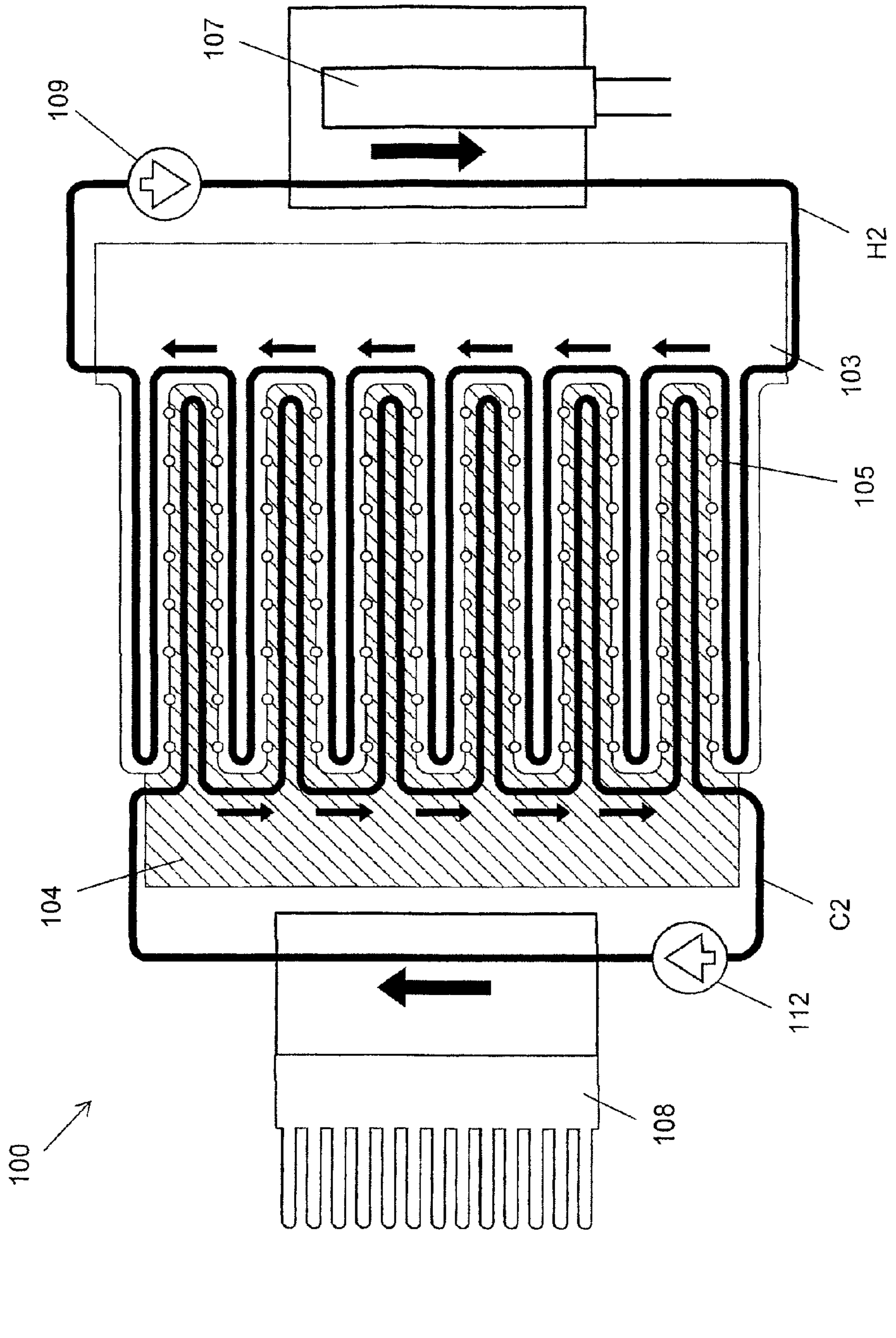
Figure 6:
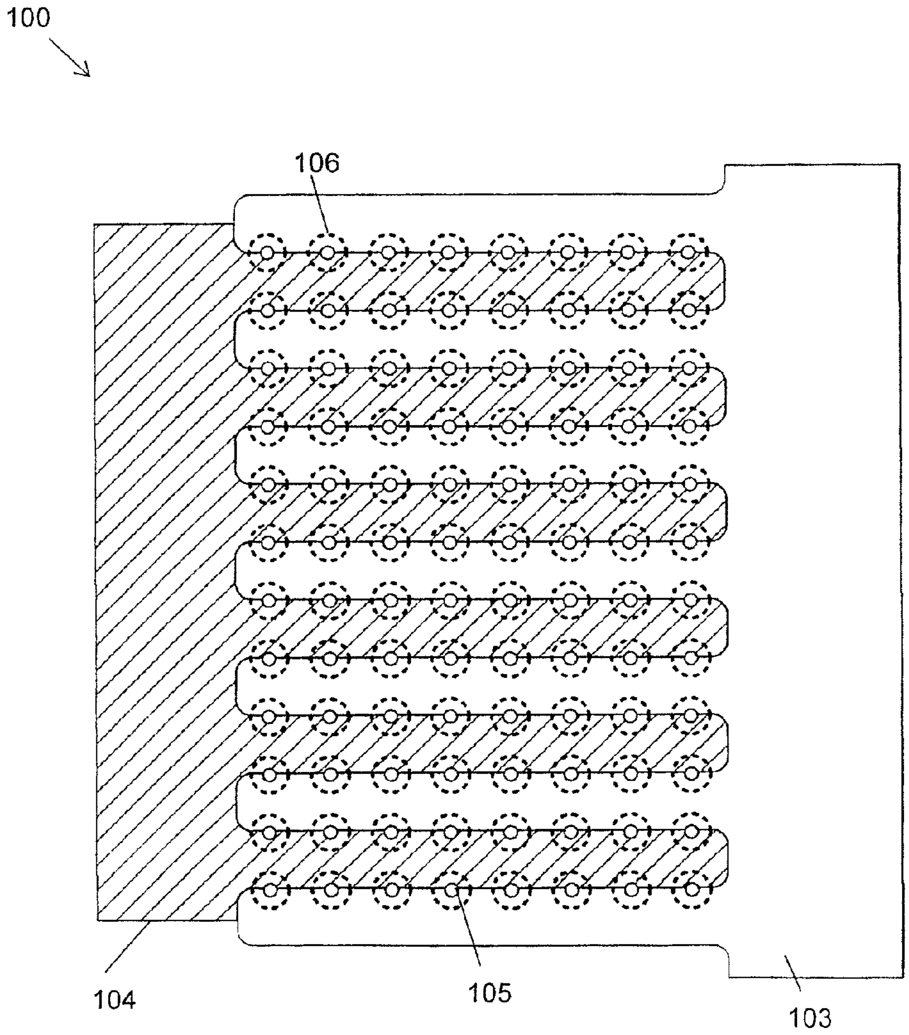

FIG. 4*a* shows a first schematic side view of a thermal control system, specifically heating elements, according to the third embodiment of the present invention;

FIG. 4*b* shows a second schematic side view of a thermal control system, specifically cooling elements, according to the third embodiment of the present invention;

FIG. 5*a* shows a first schematic plan view of the third embodiment of the present invention;

FIG. 5*b* shows a second schematic plan view of the third embodiment of the present invention; and FIG. 6 shows a further schematic view of the thermal control system, specifically well positions, according to the third embodiment of the present invention.

Figure 1:
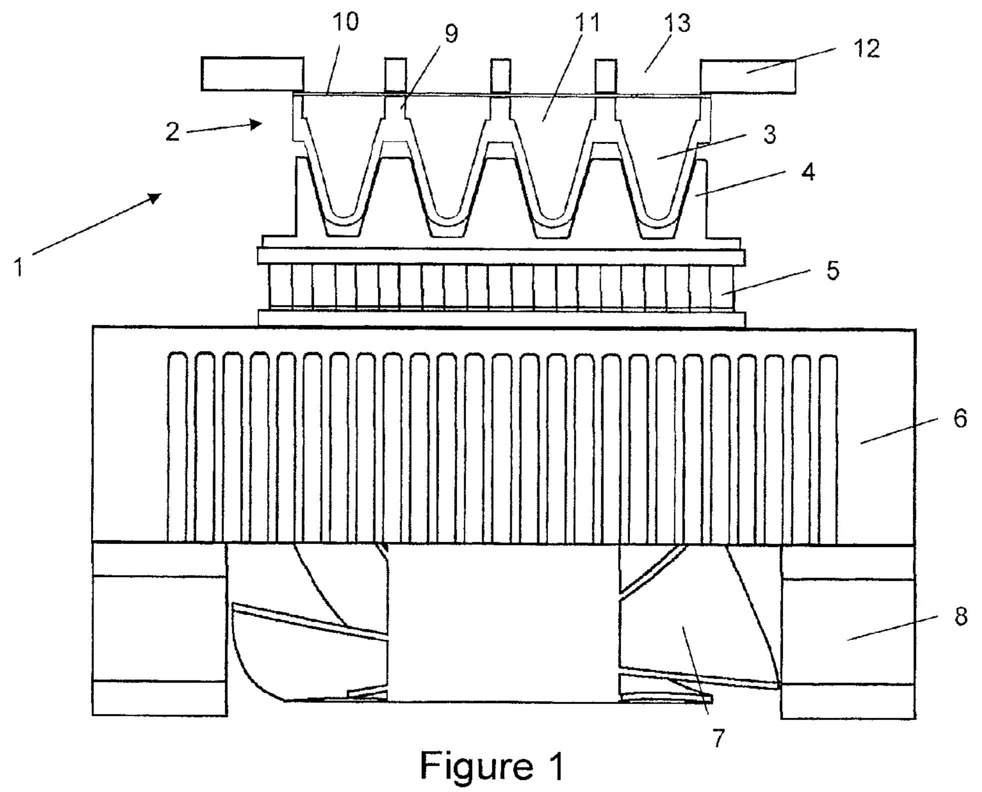
FIG. 1 shows a schematic diagram of a conventional PCR system, as known in the art.

Thus, as shown in FIG. 1, a conventional PCR system 1 includes an array 2 of vessels 3. The array 2 is positioned in a thermal mount 4 positioned on a heater/cooler 5, such as a Peltier module, of the well-known type. As is known, a Peltier module can be used to heat or cool and the Peltier module is positioned on a heat sink 6 to provide storage of thermal energy, as required. The heat sink 6 is provided with a fan 7 mounted on a fan mounting 8 on the lower side of the heat sink 6 in order to facilitate heat dissipation, as necessary.

The thermal mount 4 is made of a material with good thermal conductivity, usually metal, such as copper, and is provided with depressions, or wells, into which the vessels 3 fit so that the temperature in the vessels 3 can be controlled by controlling the temperature of the thermal mount 4. The vessels are conventionally made of polypropylene. Each vessel 3 of the array 2 is formed in the general shape of a cone and has an upper edge 9 defining a perimeter of an aperture 11 providing access to the vessel 3. The array 2 is covered by a relatively thin film 10, which is sealed to the upper edges 9 of the vessels 3 to keep the reagents and reaction products within each vessel 3. Because substantial pressures may be produced during the course of the reactions in the vessels 3, the film 10 is clamped between the edges 9 of the vessels 3 and an upper clamping member 12, to reduce the chances that the film 10 separate from the edges 9 under higher pressures and allow the reagents and/or reaction/products to escape and/or to mix. In order to allow the interiors of the vessels to be examined during the course of the reactions taking place, the film 10 is made of a transparent or translucent material and the clamping member 12 is provided with apertures 13 in register with the apertures 11 of the vessels 3 to provide visual access to the interiors of each of the vessels 3.

Figure 2:
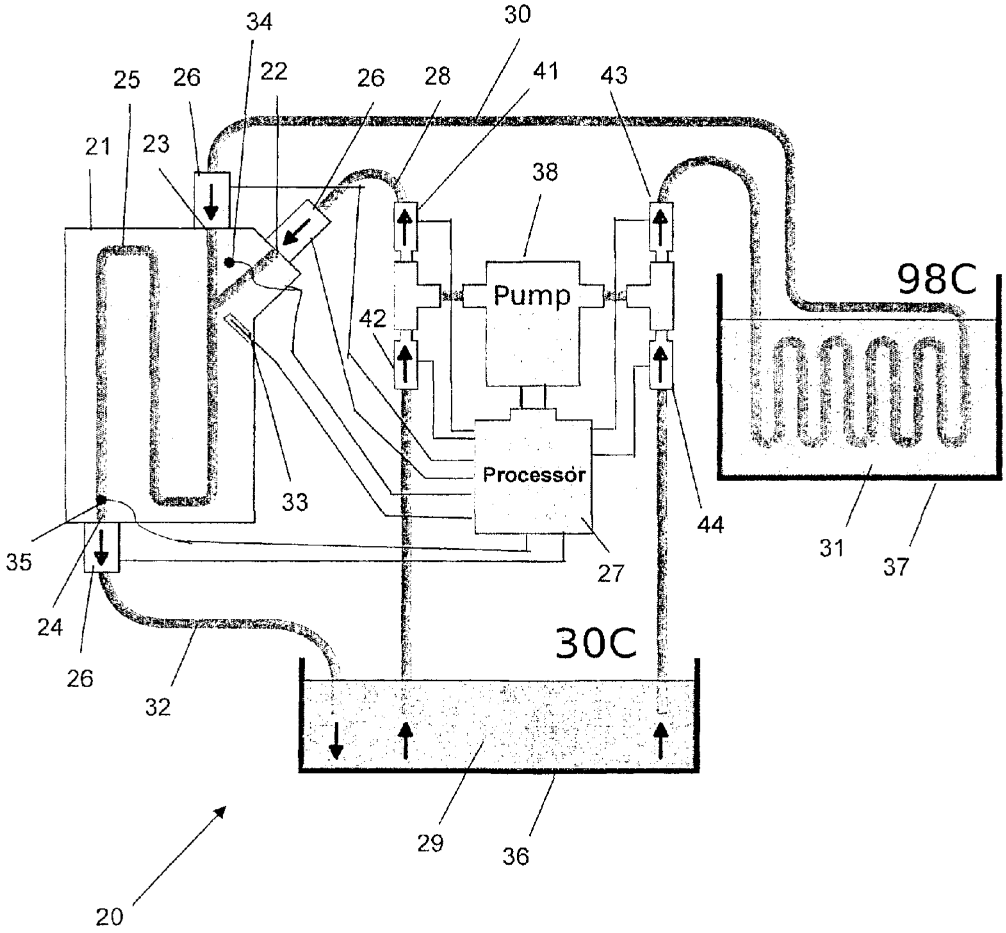
FIG. 2 shows a schematic view of a thermal control system according to one embodiment of the present invention.

FIG. 2 shows a first embodiment of a thermal control system 20 for a reaction system, according to the present invention. As here shown, a thermal block 21 forming the thermal mount of the reaction system is provided with two liquid input ports 22, 23 and one liquid output port 24. The thermal block 21 is provided with appropriate wells for receiving the vessels in which the chemical and/or biochemical reactions, such as PCR take place. However, the wells are not shown here for clarity. The thermal block 21 is provided with a liquid path 25 from the two input ports 22, 23 to the output port 24. The liquid path 25 may be of any length and configuration and is desirably one that provides substantially even thermal control of the whole of the thermal block 21. In this embodiment, as shown, the two input ports are coupled to the same liquid path 25 passing through the thermal block 21.

Controllable valves 26 are provided at each of the input and output ports and are coupled to a processor 27, which controls the valves 26. A first of the liquid input ports 22 is coupled to a cooling liquid path 28, which extends to a cooling liquid source 29. The second of the liquid input paths 23 is coupled to a heating liquid path 30, which extends to a heating liquid source 31, and the liquid output port 24 is coupled to an output liquid path 32, which extends to the cooling liquid source 29. A temperature sensor 33 is provided to measure the temperature of the thermal block 21 and an output from the temperature sensor 33 is coupled to the processor 27. Input and output flow sensors 34, 35 are also provided at the input and output ports to measure the flow rate of the liquid. The outputs of the flow sensors are also coupled to the processor 27.

The cooling liquid source 29 may comprise a cooling element, and/or can comprise a thermal ballast at a temperature lower than the lowest temperature that is required for the thermal block 21. The heating liquid source 31 can comprise a heating element and/or a thermal ballast at a temperature higher than the highest temperature that is required for the thermal block 21. For PCR systems, cooling below ambient temperature is not required, thus the cooling liquid source can be at ambient temperature. In the present case, therefore, the cooling liquid source is a tank 36 of water at or close to ambient temperature (in this case maintained at 30° C. On the other hand, the highest temperature that is required in PCR is, as mentioned above, 95° C., so the heating liquid source is maintained above this temperature, in this case, at 98° C. and comprises a tank 37 of boiling or close to boiling water. Thus, it should be appreciated that although the terms cooling and heating are used herein, the terms are relative to the maximum and minimum temperatures required for the thermal block and are not to be interpreted necessarily that heating or cooling of the liquid relative to ambient is required.

The cooling liquid path 28 takes liquid from the cooling liquid tank 36 and passes it to the cooling liquid input port 22. The heating liquid path 30 takes liquid from the cooling liquid tank 36 and passes it through a heating path in the tank 37 of hot water, whereby the liquid is heated to 98° C. before it is passed to the heating liquid input port 23. A positive displacement pump 38 is used to pump the liquid through the heating or cooling liquid paths 28, 30. The pump 38 pumps liquid through itself in either direction under the control of the processor 27 and is connected to the heating and cooling liquid paths by means of T-junctions 39, 40, respectively, which are coupled into the paths by means of valves 41, 42, 43, 44, again under the control of the processor 27. Thus, when it is required that the temperature of the thermal block 21 be lowered, valves 41 and 44 are opened and valves 42 and 43 are closed and the pump 38 pumps liquid along the cooling liquid path from the cooling liquid tank 36, through the pump 38 and into the cooling liquid input port 22. Of course, the valve 26 on cooling liquid input port 22 is open and the valve 26 on heating liquid input port 23 is closed to prevent the cooling liquid from escaping that way. Similarly, when it is required that the temperature of the thermal block 21 be increased, valves 41 and 44 are closed and valves 42 and 43 are opened and the pump 38 pumps liquid along the heating liquid path from the cooling liquid tank 36, through the pump 38, along the heating liquid path through the hot water tank 37 and into the heating liquid input port 23. Of course, the valve 26 on cooling liquid input port 22 is closed and the valve 25 on heating liquid input port 23 is open in this case.

The temperature sensor 33 measures the temperature of the thermal block 21 and provides the temperature to the processor 27. The processor 27 is programmed with the required temperature and adjusts the valves to provide either the cooling or heating liquid to the thermal block depending on whether the temperature needs to be decreased or increased. However, finer control of the temperature can be obtained by the processor by adjusting the flow rate of the liquid into the thermal block 21, by adjusting the valve 25 on the input port and the pumping rate of the pump 38. The flow rates are measured by the flow sensors 34, 35, whose outputs are also passed to the processor 27, which can thus make sure that the output flow rate is not inconsistent with the input flow rate. In this way, for example, although a required temperature may not have been reached yet, the flow rate can be diminished so that the temperature of the thermal block just reaches the desired temperature, rather than overshooting and then needing to be reduced. Alternatively, if it is desired that the temperature change be fast, then the flow rate can be maximized and then the temperature brought back slowly to the required temperature by changing the liquid passing through, but at a lower flow rate. As can be seen, therefore, much more flexibility in the control of the temperature of the thermal block is possible in this way.

Figure 3:
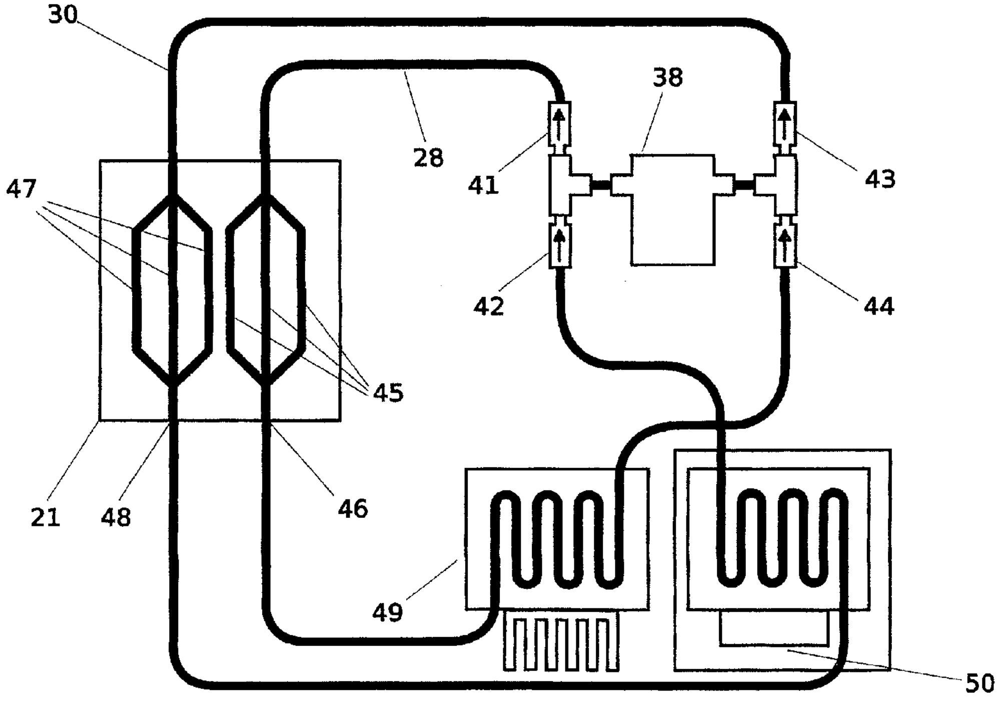
FIG. 3 shows a schematic view of a thermal control system according to a second embodiment of the present invention.

FIG. 3 shows a second embodiment of a temperature control system, similar to that of FIG. 2, and in which similar elements have similar reference numerals. In this case, the heating and cooling paths remain separate throughout the system. The cooling liquid path 28 splits into a multiplicity of cooling paths 45 within the thermal block 21 which then join together again at a single output port 46, and, similarly, the heating liquid path 30 splits into a multiplicity of heating paths 47 within the thermal block 21 and then join together at a single output port 48. Although shown separately in FIG. 3, it will be apparent that the cooling paths 45 and the heating paths 47 can be interdigitated or otherwise intertwined (whilst keeping separate) within the thermal block 21 so that the temperature thereof is made as even as possible.

Of course, as the cooling liquid passes through the thermal block 21, it heats up as it receives thermal energy, so that it is warmer as it leaves the thermal block 21 than when it enters it. Accordingly, in order to restore its temperature, the cooling liquid path 28 passes through a cooling element, such as a heatsink 49 in place of the cool water tank 36 of the previous embodiment. Similarly, the heating liquid loses thermal energy as it passes through the thermal block 21 and therefore needs to be heated again before it is input back into the thermal block. Accordingly, the heating liquid path 30 passes through a heating source, which includes a heating element 50 arranged to heat the heating liquid in the heating liquid path as it passes through the heating source. Although the heatsink 49 and the heating element 50 can be separate and independent, it can be seen that, if appropriate, they could be arranged so that the thermal energy extracted from the cooling liquid is used to heat up the heating liquid, if desired, for example, using a Peltier element.

A third embodiment of a thermal control system 100 according to the present invention is shown in FIGS. 4 to 6. In this third embodiment, the heating and cooling liquid paths are separate from each other, as in the embodiment of FIG. 2. In particular, the thermal mount 101 is separated from a hot thermal ballast 103 and a cold thermal ballast 104 by an insulator 102, with first heating and cooling liquid paths H1, C1, extending from the respective hot and cold thermal ballasts 103, 104 through the insulator 102 to the thermal mount 101.

As can best be seen in FIG. 4*a*, a first pump 110 is provided to pump heating liquid, which may be synthetic oil, around a first heating liquid path H1. The first heating liquid path H1 extends through the hot thermal ballast 103 and extends in a sinusoidal fashion through from the hot thermal ballast 103, through the insulator 102 to the thermal mount 101 and then back through the insulator 102 to the hot thermal ballast 103.

The hot thermal ballast 103 is itself heated by a hot liquid, which may also be synthetic oil, and which is pumped by a second pump 109 through the hot thermal ballast 103 along a second heating liquid path H2 which extends, also in a sinusoidal manner, through the hot thermal ballast and out to a heating block incorporating a heating element 107.

In FIG. 4*b*, the same numerals are shown for like features. There is shown a first pump 113 which is provided to pump a cooling liquid, which may be a synthetic oil, around a first cooling liquid path C1. The first cooling liquid path C1 this time extends through the cold thermal ballast 104 and extends in a sinusoidal fashion through from the cold thermal ballast 104, through the insulator 102 to the thermal mount 101 and then back through the insulator 102 to the cold thermal ballast 104.

As before, the cold thermal ballast 104 is itself cooled by a cooling liquid, which may also be synthetic oil and which is pumped by a second pump 112 through the cold thermal ballast 104 along a second cooling liquid path C2 which extends, also in a sinusoidal manner, through the cold thermal ballast and out to a cooling block incorporating a cooling element 108, such as a radiator block.

Thus, as shown in FIG. 5*a*, the first cooling and heating paths C1, H1 are shown extending through the hot and cold thermal ballasts 103 and 104. As can be seen, the hot and cold thermal ballasts 103, 104 are formed of fingers which interleave with each other so that the hot ballast fingers and cold ballast fingers are arranged with only a small separation (not shown for convenience). This separation reduces heat losses from the hot ballast to the cold ballast. Preferably the facing surfaces of the hot and cold ballasts and the separating space are arranged so as to further reduce the transfer of heat. For example the surfaces may be untreated or polished metal so as to give little radiation or absorption of infrared, with the separation being a small air gap to reduce transfer by conduction and/or convection. Alternatively the separation may be filled with an insulating material. Channels 105 are provided at intervals along the facing planes of the fingers of the hot and cold thermal ballasts 103, 104. The channels 105 are formed of grooves in each side of the hot and cold thermal ballasts 103 and 104 define the centres of the positions of the wells 106 into which the reaction vessels will fit and extend through the hot and cold thermal ballasts and through the insulator 102 to the bottom of each well 106 in the thermal mount 101, and down to the bottom of the hot and cold thermal ballasts. Thus, the channels 105 can be used for optical viewing devices, for example optical fibres, to be positioned from the bottom of the thermal system up to the bottom of each well 106 so as to view the progression of the reaction occurring in vessels located in each well 106 individually, whilst heating and/or cooling of materials in the reaction vessels is taking place. Of course, optical fibres carrying excitation light to the wells can also pass through these channels 105. It will be appreciated that if the separation between the ballasts is filled with insulating material, then the channels 105 are also provided by any suitable means through that insulating material.

Similarly, FIG. 5*b* shows the second heating and cooling liquid paths H2 and C2, with hot and cold thermal ballasts 103, 104 respectively. The respective cooling pump 112 and heating pump 109 are also shown. As can be seen, these liquid paths H2 and C2 extend through the fingers of the hot and cold thermal ballasts. In this Figure, the cold thermal ballast 104 is shown shaded for convenience of viewing, but the shading does not indicate anything more. Again, the drawing shows the fingers of the hot and cold thermal ballasts 103, 104 interleave under the well positions (not shown in this view), with the channels 105 positioned at the centre of each well position. The respective heating and cooling elements 107, 108 are also shown.

FIG. 6 shows the well positions in dotted outline 106 positioned over the channels 105 and straddling the facing planes of the interleaving fingers of the hot and cold thermal ballasts, as explained above. As before, the shading shows how the fingers of the hot and cold thermal ballasts 103, 104 interleave underneath the well positions.

It will be appreciated that although only three particular embodiments of the invention have been described in detail, various modifications and improvements can be made by a person skilled in the art without departing from the scope of the present invention. For example, it will be apparent that the expression "thermal sensor" as used herein is intended to cover any combination of components that may be used to measure temperature and can include more than one sensor with the outputs of the sensors being processed in some way to provide an appropriate temperature reading.

The invention claimed is:

1. A thermal control system for directly or indirectly controlling temperature of at least one reaction vessel adapted to contain at least one of chemical and biochemical reactions and contents thereof, the temperature being controlled in a range between at least a highest predetermined temperature and a lowest predetermined temperature, the system comprising:

- a thermal mount for receiving the at least one reaction vessel;
- at least one thermal sensor for sensing the temperature of one or more of:
  - the thermal mount;
  - the at least one reaction vessel; and
  - the contents of the at least one reaction vessel;
- a heating liquid path having a liquid therein, the heating liquid path extending between the thermal mount and a heating element capable of heating the liquid to a temperature at least as high as the highest predetermined temperature;
- a cooling liquid path having a liquid therein, the cooling liquid path extending between the thermal mount and a cooling element capable of cooling the liquid to a temperature at least as low as the lowest predetermined temperature;
- at least one pumping mechanism adapted to cause the liquid in each of the heating and cooling liquid paths to move between the thermal mount and the respective heating and cooling elements; and
- a controller coupled to the at least one thermal sensor for controlling the at least one pumping mechanism so as to move the liquid in each of the heating and cooling liquid paths to and from the thermal mount and the heating and cooling elements respectively, in accordance with at least one sensed temperature so that the temperature of the at least one reaction vessel and its contents reaches or is maintained at a control temperature for a predetermined amount of time,
- wherein the thermal mount comprises thermally conductive material having a temperature controlled by transfer of thermal energy to/from the liquid in each of the heating and cooling liquid paths, wherein the temperature of the at least one reaction vessel is controlled by transfer of thermal energy to/from the thermal mount;
- wherein the heating liquid path and the cooling liquid path comprise separate paths; and
- wherein the heating liquid path comprises a closed liquid path arranged to pass through or adjacent the heating element so that the liquid therein acquires thermal energy and to pass through or adjacent the thermal mount so that thermal energy is transferred to the thermal mount, and the cooling liquid path comprises a closed liquid path arranged to pass through or adjacent the thermal mount so that thermal energy is transferred to the cooling liquid from the thermal mount, and to pass through or adjacent the cooling element so that the liquid therein loses thermal energy.

2. The thermal control system according to claim 1, wherein the heating element comprises a hot thermal ballast, and the cooling element comprises a cold thermal ballast.

3. The thermal control system according to claim 1, wherein the at least one pumping mechanism comprises at least one pump.

4. The thermal control system according to claim 1, wherein the at least one reaction vessel forms part of an array of a plurality of reaction vessels.

5. The thermal control system according to claim 1, wherein the heating element and the cooling element are arranged to transfer thermal energy from the cooling element to the heating element.

6. The thermal control system according to claim 1, wherein the heating liquid path and the cooling liquid path are coupled to a path through or adjacent at least part of the thermal mount.

7. The thermal control system according to claim 1, wherein the temperature of the at least one reaction vessel and the contents thereof is controlled by the controller controlling flow of the liquid in each of the heating and cooling liquid paths to the thermal mount.

8. The thermal control system according to claim 7, wherein the temperature of the at least one reaction vessel and the contents thereof is controlled by the controller varying a flow rate of the liquid in each of the heating and cooling liquid paths.

9. The thermal control system according to claim 7, wherein the temperature of the at least one reaction vessel and the contents thereof is controlled by the controller stopping and starting flow of the liquid in each of the heating and cooling liquid paths.

10. The thermal control system according to claim 1, wherein the at least one reaction vessel is adapted to contain a Polymerase Chain Reaction.

11. The thermal control system according to claim 1, wherein the heating and cooling liquid paths comprise a plurality of sub-paths within the thermal mount and within the heating and cooling elements, respectively.

12. The thermal control system according to claim 1, wherein the heating and cooling elements comprise respective hot and cold thermal ballasts, respectively, having interdigitated fingers, the thermal mount is positioned above the hot and cold ballasts such that the at least one reaction vessel, when positioned on the thermal mount, substantially straddles across a boundary between two of the interdigitated fingers.

13. The thermal control system according to claim 1, further comprising a channel extending through the thermal mount from a location where the at least one reaction vessel is positioned to an external location of the thermal control system to allow optical sensing means to optically sense a reaction occurring in the at least one reaction vessel.

14. A method of directly or indirectly controlling temperature of at least one reaction vessel adapted to contain at least one of chemical and biochemical reactions and contents thereof, the at least one reaction vessel being mounted on a thermal block, the temperature being controlled in a range between at least a highest predetermined temperature and a lowest predetermined temperature, the method comprising:

sensing the temperature of one or more of:

the thermal block;

the at least one reaction vessel; and the contents of the at least one reaction vessel; and selectively pumping a heating liquid along a heating liquid path extending between the thermal block and a heating element capable of heating the liquid to a temperature at least as high as the highest predetermined temperature; and selectively pumping a cooling liquid along a cooling liquid path extending between the thermal block and a cooling element capable of cooling the liquid to a temperature at least as low as the lowest predetermined temperature, in accordance with the sensed temperature so that the temperature of the at least one reaction vessel and the contents thereof reaches or is maintained at a control temperature for a predetermined amount of time, wherein the thermal block comprises a thermally conductive material, and the method further comprises:

controlling a temperature of the thermal mount by transferring thermal energy to/from the liquid in each of the heating and cooling liquid paths, so that the temperature of the at least one reaction vessel is controlled by transfer of thermal energy to and from the thermal block;

wherein the heating liquid path and the cooling liquid path comprise separate paths; and wherein the heating liquid path comprises a closed liquid path arranged to pass through or adjacent the heating element so that the liquid therein acquires thermal energy and to pass through or adjacent the thermal block so that thermal energy is transferred to the thermal block, and the cooling liquid path comprises a closed liquid path arranged to pass through or adjacent the thermal block so that thermal energy is transferred to the cooling liquid from the thermal block, and to pass through or adjacent the cooling element so that the liquid therein loses thermal energy.

15. The method according to claim 14, wherein the at least one reaction vessel forms part of an array of a plurality of reaction vessels.

16. The method according to claim 14, wherein the heating and cooling elements comprise hot and cold thermal ballasts, respectively, having interdigitated fingers, the method comprising positioning the thermal block above the hot and cold thermal ballasts and positioning the at least one reaction vessel on the thermal mount such that the at least one reaction vessel substantially straddles across a boundary between two of the interdigitated fingers.

17. The method according to claim 14, wherein the heating liquid path and the cooling liquid path are coupled to a path through or adjacent at least part of the thermal block.

18. The method according to claim 14, wherein the heating and cooling liquid paths comprise a plurality of sub-paths within the thermal block and within the heating and cooling elements, respectively.

19. The method according to claim 14, wherein the temperature of the at least one reaction vessel and the contents thereof is controlled by controlling flow of the liquid in each of the heating and cooling liquid paths to the thermal block.

20. The method according to claim 19, wherein the temperature of the at least one reaction vessel and the contents thereof is controlled by varying a flow rates of the liquid in each of the heating and cooling liquid paths.

21. The method according to claim 19, wherein the temperature of the at least one reaction vessel and the contents thereof is controlled by stopping and starting flow of the liquid in each of the heating and cooling liquid paths.

22. The method according to claim 14, wherein the heating element and the cooling element transfer thermal energy from the cooling element to the heating element.

* * * * *